United States Patent [19]

Wang et al.

[11] Patent Number: 4,882,374
[45] Date of Patent: Nov. 21, 1989

[54] DIOXAPHOSPHORINANE COMPOUNDS AND POLYOLEFIN COMPOSITIONS STABILIZED THEREWITH

[75] Inventors: Richard H. S. Wang; Garry L. Myers, both of Kingsport, Tenn.

[73] Assignee: Eastman Kodak Company, Rochester, N.Y.

[21] Appl. No.: 306,130

[22] Filed: Feb. 6, 1989

[51] Int. Cl.$^4$ ............................................... C08K 5/49
[52] U.S. Cl. ...................................... 524/117; 558/85
[58] Field of Search ............................ 524/117; 558/85

[56] References Cited

U.S. PATENT DOCUMENTS 3,441,633  4/1969  Friedman .............................. 105/88
3,467,733  9/1969  Dever et al. .......................... 401/200
3,592,858  7/1971  Brimer ................................. 568/580
3,714,302  1/1973  Dever et al. .......................... 558/85

OTHER PUBLICATIONS

C.A. 70:4150s, French Patent 1,501,427 (abstract).

Primary Examiner—John Kight, III
Assistant Examiner—Kriellion Morgan
Attorney, Agent, or Firm—J. Frederick Thomsen; William P. Heath, Jr.

[57] ABSTRACT

Disclosed are novel cyclic phosphite compounds having the formula

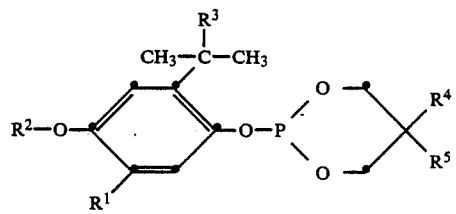

wherein $R^1$ is hydrogen, alkyl or aralkyl; $R^2$ is hydrogen or alkyl; $R^3$ is alkyl or aryl; and $R^4$ and $R^5$ each is alkyl. Also disclosed are polyolefin compositions stabilized with one or more of the above compounds.

6 Claims, No Drawings

DIOXAPHOSPHORINANE COMPOUNDS AND POLYOLEFIN COMPOSITIONS STABILIZED THEREWITH

This invention concerns certain novel dioxaphosphorinane compounds and polyolefine materials stabilized therewith. More specifically, this invention concerns certain storage-stable, cyclic phosphites and polyolefin materials stabilized against thermally-induced oxidative degradation by the presence therein of at least one of the cyclic phosphites.

Synthetic polymeric materials such as polyolefins, particularly propylene, require stabilization against thermal degradation to prevent significant changes in the properties of the polymeric material during melt processing. For example, without adequate stabilization, the melt-flow rate of polypropylene changes significantly during its extrusion in the compounding of various formulations and products. Various cyclic phosphites (and the use thereof in polyolefins) are well-known. See, for example, U.S. Pat. Nos. 3,441,633, 3,467,733, 3,592,858 and 3,714,302 and French Patent 1,501,427. Many of these known cyclic phosphite compounds possess moderate to poor storage stability which imparts poor handling properties and causes their effectiveness as polyolefin stabilizers to diminish when they are stored over a period of time, especially in areas of high humidity. The novel cyclic phosphites provided by our invention exhibit excellent storage stability and are effective process stabilizers for polyolefins. Our novel cyclic phosphites are liquids at normal ambient temperatures, a characteristic which is advantageous for their preparation and use.

The cyclic phosphites of this invention have the general formula

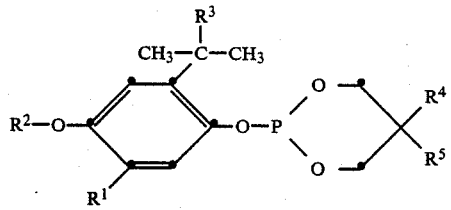

wherein
$R^1$ is hydrogen, alkyl or aralkyl;
$R^2$ is hydrogen or alkyl;
$R^3$ is alkyl or aryl;
$R^4$ and $R^5$ each is alkyl.

Examples of the alkyl groups represented by $R^1$, $R^2$, $R^3$, $R^4$ and $R^5$ include alkyl containing up to about 8 carbon such as methyl, ethyl, propyl, 2-propyl, butyl, 2-butyl, 2-methyl-2-propyl, pentyl, 2-pentyl, hexyl, 2-ethylhexyl, 2,4,4-trimethyl-2-pentyl. The alkyl groups represented by $R^1$, $R^2$, $R^3$, $R^4$ and $R^5$ preferably contain up to 4 carbon atoms. The aryl group represented by $R^3$ and the aryl moiety of the aralkyl radical represented by $R^1$ may be unsubstituted phenyl or phenyl substituted with 1 or 2 groups selected from lower, i.e., containing up to about 4 carbon atoms, alkyl, lower alkoxy or halogen, e.g., chlorine or bromine. The alkyl moiety of the aralkyl groups typically is lower alkyl. The aryl group represented by $R^3$ and the aryl moiety of the aralkyl radical represented by $R^1$ preferably are unsubstituted phenyl.

The compounds of formula (I) may be prepared by reacting a cyclic phosphite chloride having the formula

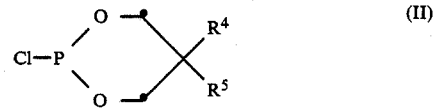

with an alkylated hydroquinone or mono-alkyl ether of an alkylated hydroquinone compound having the formula

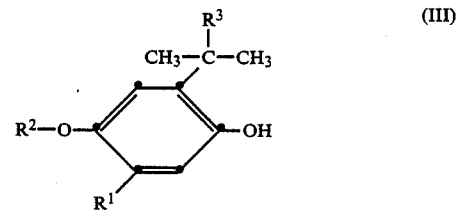

according to known procedures, wherein $R^1$, $R^2$, $R^3$, $R^4$ and $R^5$ are defined above. Examples of the compounds of formula (III) are 2-(1,1-dimethylethyl)-4-methoxyphenol, 4-butoxy-2-(1,1-dimethylpropyl)-phenol, 2-(α,α-dimethylbenzyl)-4-ethoxyphenol, and the like. The cyclic phosphite chloride compounds of formula (II) may be obtained according to known procedures such as those described in the references cited hereinabove.

The compounds of our invention which are preferred have the formula

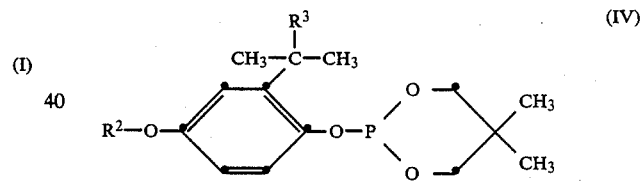

wherein $R^2$ and $R^3$ each is methyl or ethyl.

The preparation of the dioxaphosphorinane compounds of our invention is further illustrated by the following example.

EXAMPLE 1

Phosphorus trichloride (1.25 mol) is added over a period of 90 minutes to a solution of neopentyl glycol (1.25 mol) in 750 mL of toluene at 0° C. The reaction mixture is stirred at 0° to 5° C. for an additional 60 minutes and then is heated to 90° C. and 2-(1,1-dimethyl-yl-ethyl)-4-methoxyphenol (0.625 mol) is added over 10 to 15 minutes. The reaction is heated to and held at reflux for 30 minutes and toluene is removed to a head temperature of 110° C. The mixture is held at 110° C. for 4 hours with nitrogen sparging. The remaining toluene is removed to 120° C. head temperature and 170° C. pot temperature. Excess 2-chloro-5,5-dimethyl-1,3,2,-dioxaphosphorinane is removed at 125° C. head temperature under a vacuum of 10 mm. (FDMS MW=168) The product, 2-chloro-5,5-dimethyl-1,3,2-dioxaphosphorinane, is collected by distillation at 9 mm and 198° C. head temperature. It is obtained in a yield of 95% and a purity of 100% by gas chromatography analysis.

FDMS MW=312; Viscosity: 500±5 cps at 27° C.

Elemental analysis, Calc. for $C_{16}H_{25}O_4P$: C,61.54; H,8.01 Found: C,60.31; H,8.04

The cyclic phosphite compounds of formula (I) may be used in a wide variety of polyolefin materials which are susceptible to degradation upon exposure to heat and/or radiation including both visible and ultraviolet light. Examples of such materials include homo- and co-polymers of α-olefins such as polyethylene, polypropylene, polybutene, poly-3-methylbutene and ethylene-propylene copolymers and ethylene-vinyl acetate copolymers. The preferred stabilized compositions of our invention comprise homo- and co-polymers of α-olefins of 2 to 4 carbon atoms, especially polypropylene, containing a stabilizing amount of one or more of the compounds of formula (I).

The concentration of the phosphite compound in the polymeric material which will effectively inhibit polymer degradation can vary considerably depending on the particular polymer being stabilized and the end use for which the stabilized polymeric material is designed. Generally, concentration in the range of 0.001 to 5.0 weight percent may be used with concentrations of about 0.01 to 0.5 being most common. The phosphite stabilizers provided by this invention typically will be used in combination with other conventional stabilizers such as phenolic antioxidants, polyvalent salts of organic acids and thioethers. In addition, other additives, such as plasticizers, lubricants, emulsifiers, antistatic agents, flame retardant agents, pigments and fillers, commonly used in formulating commercial polymeric compositions may be present.

The phosphite stabilizer may be incorporated into the polymeric materials by conventional blending techniques. For example, the stabilizer may be added directly to a melt of the polymer on a roll mill to distribute the phosphite compound uniformly throughout the polymer. Alternatively, the phosphite compound may be dry-blended with a finely-divided form of the polymer such as pellets and then the dry mix can be mixed further in and extruded from an extruder.

The effectiveness of 2-[2-(1,1-dimethylethyl)-4-methoxyphenoxy]-5,5-dimethyl-1,3,2-dioxaphosphorinane (Compound A) as a processing stabilizer was evaluated and compared to the effectiveness of tris(4-nonylphenyl) phospite (Compound B; Naugard PHR) and tris[2,4-bis(1,1-dimethylethyl)phenyl]phosphite (Compound C; Mark 2112), two commercial products commonly used as processing inhibitors for polypropylene. Samples of polypropylene containing 0.10 phr (parts by weight per 100 parts by weight polypropylene) calcium stearate, 0.20 phr dilauryl thiodipropionate, 0.05 phr 2,2-bis[[3-[3,5-bis(1,1-dimethylethyl)-4-hydroxyphenyl]-1-oxopropoxy]-methyl]-1,3-propanediyl 3,5-bis(1,1-dimethylethyl)-4-hydroxybenzenepropanoate (Irganox 1010 stabilizer) and 0.025 phr of phosphite compound A, B or C are prepared by shaking the additives and polypropylene pellets together in a plastic bag and then blending the dry mix in and extruding each sample from a Brabender single screw rod extruder at 260° C. Each polypropylene sample was extruded five times. After each extrusion, the melt-flow rate (ASTM Method D 1238, Procedure A, Condition E; g/10 minutes), yellowness index (ASTM Method D 1925; b value) and oven life (ASTM D3012; 150° C., hours) are determined for each sample. Test bars (2 inch×0.5 inch×0.05 inch thick) compression molded at about 100° C. were used in determining yellowness and oven life. The inhibiting effect of each phosphite compound on the thermal degradation of the polypropylene is shown in Table I.

TABLE I

| Extruded Sample | Compound A | Compound B | Compound C |
|---|---|---|---|
| First Extrusion | | | |
| Melt Flow Rate | 7.0 | 8.4 | 7.6 |
| Yellowness | 0.22 | 1.42 | 0.53 |
| Oven Life | 1329 | 1248 | 1291 |
| Second Extrusion | | | |
| Melt Flow Rate | 7.0 | 8.8 | 8.2 |
| Yellowness | 0.60 | 2.78 | 1.00 |
| Oven Life | 1152 | 1276 | 1262 |
| Third Extrusion | | | |
| Melt Flow Rate | 7.1 | 9.3 | 8.7 |
| Yellowness | 0.85 | 3.31 | 1.92 |
| Oven Life | 1305 | 1200 | 1272 |
| Fourth Extrusion | | | |
| Melt Flow Rate | 7.9 | 10.1 | 9.4 |
| Yellowness | 1.29 | 4.24 | 2.25 |
| Oven Life | 1041 | 1291 | 1272 |
| Fifth Extrusion | | | |
| Melt Flow Rate | 7.7 | 11.4 | 10.4 |
| Yellowness | 1.52 | 4.90 | 3.00 |
| Oven Life | 1289 | 1224 | 1243 |

The invention has been described in detail with particular reference to preferred embodiments thereof, but it will be understood that variations and modifications will be effected within the spirit and scope of the invention.

We claim:

1. A stabilized composition comprising a poly-α-olefin susceptible to degradation upon exposure to heat and/or radiation containing a stabilizing amount of a compound having the formula

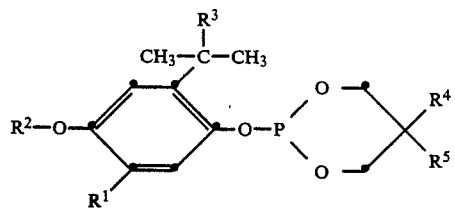

wherein
$R^1$ is hydrogen, alkyl or aralkyl;
$R^2$ is hydrogen or alkyl;
$R^3$ is alkyl or aryl; and
$R^4$ and $R^5$ each is alkyl.

2. A stabilized composition according to claim 1 wherein the polyolefin is a polymer of an α-olefin having 2 to 4 carbon atoms and wherein
$R^1$ is hydrogen;
$R^2$ is hydrogen or alkyl of 1 to 4 carbon atoms;
$R^3$ is alkyl of 1 to 4 carbon atoms or phenyl; and
$R^4$ and $R^5$ each is alkyl of 1 to 4 carbon atoms.

3. A stabilized composition according to claim 1 comprising polypropylene susceptible to degradation upon exposure to heat and/or radiation containing a stabilizing amount of a compound having the formula

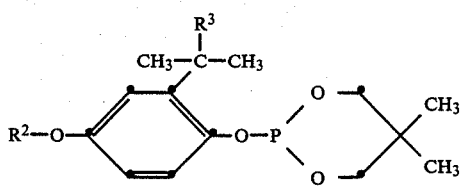

wherein $R^2$ and $R^3$ are methyl or ethyl.

4. A compound having the formula

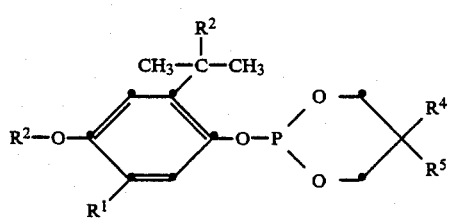

wherein
  $R^1$ is hydrogen, alkyl or aralkyl;
  $R^2$ is hydrogen or alkyl;
  $R^3$ is alkyl or aryl; and
  $R^4$ and $R^5$ each is alkyl.

5. A compound according to claim 4 wherein
  $R^1$ is hydrogen;
  $R^2$ is hydrogen or alkyl of 1 to 4 carbon atoms;
  $R^3$ is alkyl of 1 to 4 carbon atoms or phenyl; and
  $R^4$ and $R^5$ each is alkyl.

6. A compound having the formula

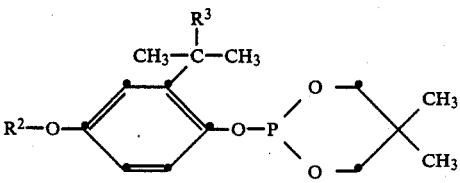

wherein $R^2$ and $R^3$ are methyl or ethyl.

* * * * *